US012630717B2

(12) United States Patent
Tamper et al.

(10) Patent No.: US 12,630,717 B2
(45) Date of Patent: May 19, 2026

(54) WOOD-DERIVED LIGNIN COMPOSITION

(71) Applicant: UPM-KYMMENE CORPORATION, Helsinki (FI)

(72) Inventors: Juha Tamper, Levanen (FI); Sami Turunen, Lappeenranta (FI); Vilho Nissinen, Vehkataipale (FI); Nina Heiming, Xanten (DE); Lisa Weigand, Wiesbaden (DE); Mauno Miettinen, Lappeenranta (FI); Moritz Leschinsky, Leipzig (DE)

(73) Assignee: UPM-KYMMENE CORPORATION, Helsinki (FI)

( * ) Notice: Subject to any disclaimer, the term of this patent is extended or adjusted under 35 U.S.C. 154(b) by 774 days.

(21) Appl. No.: 18/009,208

(22) PCT Filed: Jun. 9, 2021

(86) PCT No.: PCT/FI2021/050432
§ 371 (c)(1),
(2) Date: Dec. 8, 2022

(87) PCT Pub. No.: WO2021/250327
PCT Pub. Date: Dec. 16, 2021

(65) Prior Publication Data
US 2023/0257586 A1 Aug. 17, 2023

(30) Foreign Application Priority Data
Jun. 12, 2020 (FI) ...................................... 20205613

(51) Int. Cl.
C08H 8/00 (2010.01)
C08L 97/00 (2006.01)
C12P 19/14 (2006.01)

(52) U.S. Cl.
CPC .............. C08L 97/005 (2013.01); C08H 8/00 (2013.01); C12P 19/14 (2013.01); C12P 2201/00 (2013.01)

(58) Field of Classification Search
None
See application file for complete search history.

(56) References Cited

U.S. PATENT DOCUMENTS 5,393,804 A * 2/1995 George ................... C08L 29/04
524/53
2009/0098618 A1* 4/2009 Burke ..................... C12P 19/02
435/99

(Continued)

FOREIGN PATENT DOCUMENTS

JP        S62288643 A    12/1987
JP        S62288644 A    12/1987

(Continued)

OTHER PUBLICATIONS

Isolation of high quality lignin as a by-product from ammonia percolation pretreatment of poplar woods, Bouxin et al., Bioresource Technology, 162, (2014), 236-242 (Year: 2014).*

(Continued)

*Primary Examiner* — Peter A Salamon
(74) *Attorney, Agent, or Firm* — Nixon Peabody LLP

(57) ABSTRACT

A wood-derived lignin composition is disclosed. The wood-derived lignin composition comprises: —acid-insoluble lignin in an amount of 80-90 weight-% based on the total dry matter content of the lignin composition, wherein the average molecular weight of the lignin is 5000-15000 Da; —carbohydrates in an amount of 1.5-15 weight-% based on the total dry matter content of the lignin composition; —nitrogen in an amount of 0.2-1.5 weight-% based on the total dry matter content of the lignin composition; and (Continued)

wherein weight ratio of oxygen to carbon is at least 0.5 Further is disclosed a method for producing the wood-derived lignin composition.

16 Claims, 1 Drawing Sheet

(56) References Cited

U.S. PATENT DOCUMENTS

| | | | |
|---|---|---|---|
| 2015/0075254 A1 | 3/2015 | Sakuma et al. | |
| 2019/0112623 A1* | 4/2019 | Turunen | C12P 19/02 |
| 2021/0323989 A1 | 10/2021 | Miettinen | |

FOREIGN PATENT DOCUMENTS

| | | |
|---|---|---|
| JP | H08503985 A | 4/1996 |
| JP | 2002236361 A | 8/2002 |
| JP | 2014031494 A | 2/2014 |
| JP | 2018516292 A | 6/2018 |
| JP | 2019512206 A | 5/2019 |
| WO | 2016124821 A1 | 8/2016 |
| WO | 2016193535 A1 | 12/2016 |
| WO | 2017162923 A1 | 9/2017 |

OTHER PUBLICATIONS

Office Action in Japanese Patent Application JP2022-575679 with English Translation, mailed May 27, 2025, (8 pages).

Rahikainen J. et al., Inhibition of Enzymatic Hydrolysis by Residual Lignins From Softwood-Study of Enzyme Binding and Inactivation on Lignin-Rich Surface, Biotechnology and Bioengineering, 2011. vol. 108, pp. 2823-2834.

Nakagame S. et al., The isolation, characterization and effect of lignin isolated from steam pretreated Douglas-fir on the enzymatic hydrolysis of cellulose, Bioresource Technology, 2010. vol. 102, pp. 4507-4517.

Tolbert A. et al., Characterization and analysis of the molecular weight of lignin for biorefining studies, Biofuels, Bioproducts and Biorefining, 2014, vol. 8, pp. 836-856.

Ju X. et al., An advanced understanding of the specific effects of xylan and surface lignin contents on enzymatic hydrolysis of lignocellulosic biomass, Bioresource Technology, 2013. vol. 132, pp. 137-145.

Bouxin Florent P. et al, Isolation of high quality lignin as a by-product from ammonia percolation pretreatment of poplar wood, Bioresource Technology, vol. 162, Mar. 26, 2014, pp. 236-242.

Search Report issued in Patent Application No. FI 20205613, mailed Jan. 15, 2021 (2 pp.).

International Search Report in International Patent Application No. PCT/FI2021/050432, mailed Sep. 23, 2021 (6 pp.).

* cited by examiner

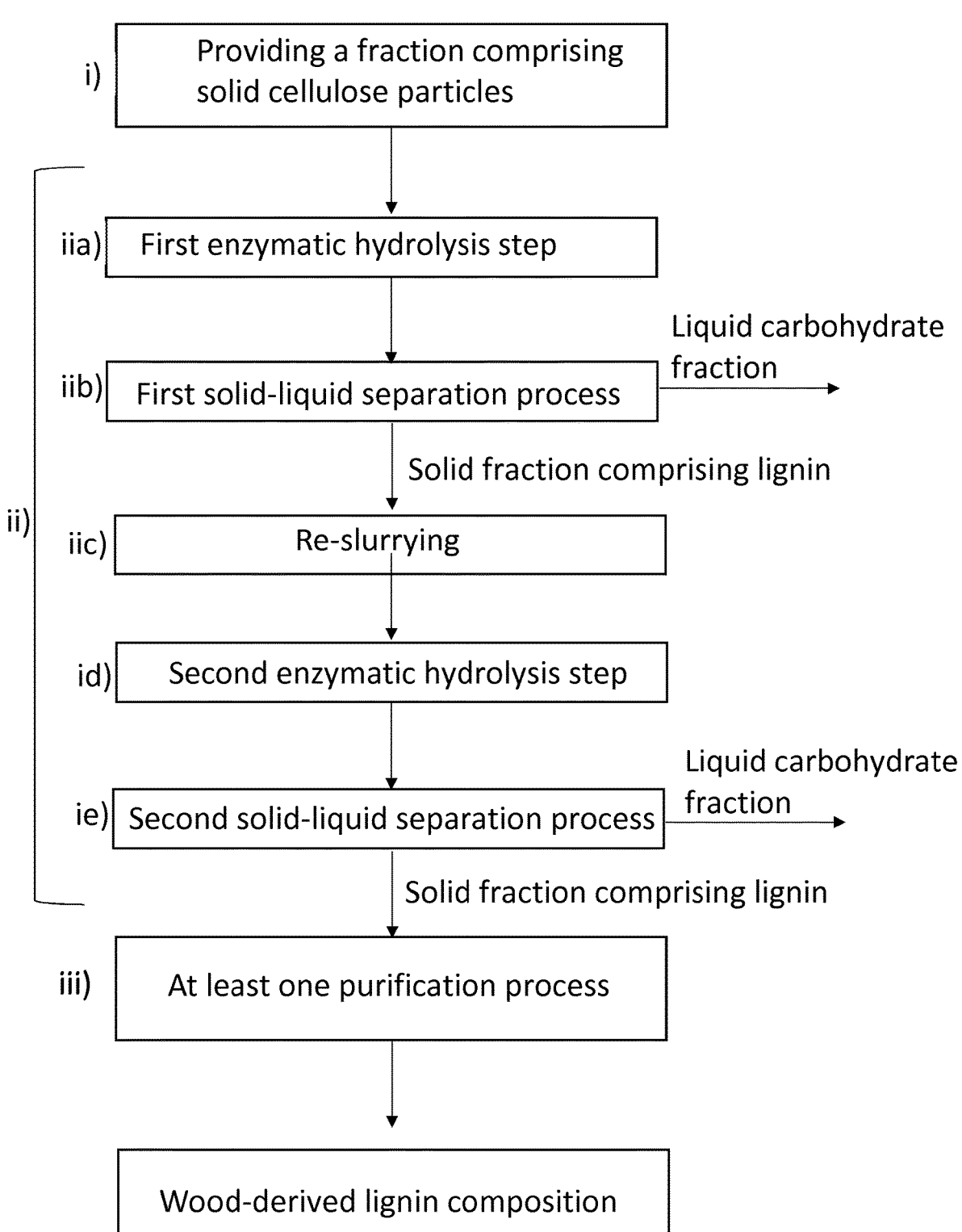

1

WOOD-DERIVED LIGNIN COMPOSITION

CROSS-REFERENCE TO RELATED APPLICATIONS

This application is a U.S. National Phase Entry of International Application No. PCT/FI2021/050432, filed on Jun. 9, 2021, which claims the benefit of and priority to FI application No. 20205613, filed Jun. 12, 2020, each of which is hereby incorporated by reference herein in its entirety.

TECHNICAL FIELD

The present disclosure relates to a wood-derived lignin composition and the use thereof. The present disclosure further relates to a method for producing a wood-derived composition.

BACKGROUND

Different methods are known for converting biobased raw material, such as lignocellulosic biomass, into a liquid stream of various components. Being able to provide sufficiently pure lignin composition with properties suitable for further applications has still remained as a task for researchers.

SUMMARY

A wood-derived lignin composition is disclosed. The wood-derived lignin composition may comprise:—acid-insoluble lignin in an amount of 80-90 weight-% based on the total dry matter content of the lignin composition, wherein the average molecular weight of the lignin is 5000-15000 Da;—carbohydrates in an amount of 1.5-15 weight-% based on the total dry matter content of the lignin composition;—nitrogen in an amount of 0.2-1.5 weight-% based on the total dry matter content of the lignin composition; and the weight ratio of oxygen to carbon is at least 0.5.

Further is disclosed a method for producing a wood-derived lignin composition. The method may comprise:

i) providing a wood-based feedstock originating from wood-based raw material and comprising wood chips, and subjecting the wood-based feedstock to pretreatment to form a fraction comprising solid cellulose particles, wherein the total dry matter content of the fraction comprising solid cellulose particles is 8-20 weight-%, and wherein at most 3 weight-% of the wood shives in the fraction comprising solid cellulose particles are wider than 1 mm as determined by the Somerville method;

ii) subjecting the fraction comprising solid cellulose particles from i) to an enzymatic hydrolysis process, wherein the enzymatic hydrolysis process comprises:

iia) subjecting the fraction comprising solid cellulose particles to a first enzymatic hydrolysis step for 8-72 hours to form a first hydrolysis product;

iib) separating the first hydrolysis product into a solid fraction comprising lignin and a liquid carbohydrate fraction by a first solid-liquid separation process;

iic) re-slurrying the separated solid fraction comprising lignin from iib) by mixing it with a liquid;

iid) subjecting the re-slurried solid fraction comprising lignin to a second enzymatic hydrolysis step for 8-72 hours to form a second hydrolysis product;

iie) separating the second hydrolysis product into a solid fraction comprising lignin and a liquid carbohydrate fraction a by second solid-liquid separation process;

iii) subjecting the solid fraction comprising lignin from the enzymatic hydrolysis process of ii) to at least one purification process to provide the lignin composition.

Further is disclosed a wood-derived lignin composition obtainable by the method as disclosed in the current specification.

Further is disclosed the use of the wood-derived lignin composition as disclosed in the current specification for the production of a composite, a filler material, an adhesive, a paint, or a resin.

BRIEF DESCRIPTION OF THE DRAWINGS

The accompanying drawing, which is included to provide a further understanding of the embodiments and constitute a part of this specification, illustrates an embodiment. In the drawing:

FIG. 1 presents a flow chart of one embodiment of the method for producing a wood-derived lignin composition.

DETAILED DESCRIPTION

A wood-derived lignin composition is disclosed. The wood-derived lignin composition may comprise:—acid-insoluble lignin in an amount of 80-90 weight-% based on the total dry matter content of the lignin composition, wherein the average molecular weight of the lignin is 5000-15000 Da;—carbohydrates in an amount of 1.5-15 weight-% based on the total dry matter content of the lignin composition; and—nitrogen in an amount of 0.2-1.5 weight-% based on the total dry matter content of the lignin composition. The weight ratio of oxygen to carbon may be at least 0.5.

Further is disclosed a method for producing a wood-derived lignin composition. The method may comprise:

i) providing a wood-based feedstock originating from wood-based raw material and comprising wood chips, and subjecting the wood-based feedstock to pretreatment to form a fraction comprising solid cellulose particles, wherein the total dry matter content of the fraction comprising solid cellulose particles is 8-20 weight-%, and wherein at most 3 weight-% of the wood shives in the fraction comprising solid cellulose particles are wider than 1 mm as determined by the Somerville method;

ii) subjecting the fraction comprising solid cellulose particles from i) to an enzymatic hydrolysis process, wherein the enzymatic hydrolysis process comprises:

iia) subjecting the fraction comprising solid cellulose particles to a first enzymatic hydrolysis step for 8-72 hours to form a first hydrolysis product;

iib) separating the first hydrolysis product into a solid fraction comprising lignin and a liquid carbohydrate fraction by a first solid-liquid separation process;

iic) re-slurrying the separated solid fraction comprising lignin from iib) by mixing it with a liquid;

iid) subjecting the re-slurried solid fraction comprising lignin to a second enzymatic hydrolysis step for 8-72 hours to form a second hydrolysis product;

iie) separating the second hydrolysis product into a solid fraction comprising lignin and a liquid carbohydrate fraction a by second solid-liquid separation process;

iii) subjecting the solid fraction comprising lignin from the enzymatic hydrolysis process of ii) to at least one purification process to provide the lignin composition.

Further is disclosed a wood-derived lignin composition obtainable by the method as disclosed in the current specification. In one embodiment, the wood-derived lignin composition obtainable by the method as disclosed in the current specification is the wood-derived lignin composition as disclosed in the current specification. I.e. the wood-derived lignin composition disclosed in the current specification may be produced by the method as disclosed in the current specification.

Further is disclosed the use of the wood-derived lignin composition as disclosed in the current specification for the production of a composite, a filler material, an adhesive, a paint, or a resin. The "Somerville method" as used in this specification follows the standard Tappi T 275 sp-07 with the following deviation: According to Tappi T 275 sp-07, the amount of sample added onto a flat screen is 50 g of oven dry sample. In the "Somerville method" as used in this specification, 50 g of sample (total solids) is added onto Somerville 1.0 mm screen after cold disintegration, but the total suspended solid content of the sample depends on the amount of solubles in the sample. The measurement according to the Somerville method may be conducted in the following manner: Original wet sample is weighed to get 50 g of dry sample (TS) to cold disperse. The cold disperse may be conducted as follows:

The wet sample, calculated to be 50 g of the oven dry material, is moved to a disperse cup and then 20±5° C. water is added to get 2000 ml disperse volume. Sample total dry matter (total solids TS) is determined in an oven at 60° C. and total suspended solids is determined based on the following: The solids content of a sample is determined as the quantity of the solid material compared to the total dry matter (quantity of solid+soluble). Warm (approx. 50° C.) slurry of about 7% total suspended solids (corresponds often to ~10% totals solids) is prepared and sample is extracted for half an hour while stirring. The formed slurry is filtered and the solid substances will be washed away from the cake. When filtering the sample in accordance with the method, only the solid will remain in the filter. The sample will be filtered through the pre-weighed filter paper. When necessary, the filtrate may be taken for storage and wash the filtrated cake three times with a large amount of warm tap water (approx. 50° C.). The cake is dried at least overnight in the oven at over 60° C. (dry to constant weight). The sample concentration of solids is calculated by using the following formula:

$$X = \frac{(a-b)}{c}$$

where
X=solid, total suspended solids (TSS), %
a=filter and weight of the residue, g
b=filter weight, g
c=quantity of the sample, g
Based on the total solids, the necessary sample amount is calculated for analysis.

After the cold disintegration, the 1.0 mm flat screen is adjusted. All the dispersed sample (cold disintegration) is flushed on the 1.0 mm sieve and the timer is started. End after 20 minutes. The flat screen is moved to a collecting container and flushed carefully so that all the shives are washed away. The shives remaining on the sieve are taken and flushed through a pre-weighted filter paper. The shives are dried in a drying oven overnight at 105° C.±2° C. The shives are refrigerated in a desiccator and weighed with an accuracy of 1 mg.

The amount of shives may then be calculated as a percentage of the dry weight of the added suspended solid weigh:

Somerville(Primary shives) %=m(shives+filter paper)−m(filter paper)mTSS*100, where Somerville (Primary shives)=Somerville primary shive content
m(shives+filter paper)=the weight of the shives and the filter paper, g
m(filter paper)=the weight of the filter paper, g
mTSS=oven (60° C.) dry total suspended solids of the sample, g
mTSS can be calculated when total suspended solids have been measured based on the above described method and thus the percentage of suspended solids is known in the sample (TSS %).

mTSS=msample×TSS % msample=the weight of the sample for Somerville analysis, g
SS %=total suspended solids of the sample, %
The wood-derived lignin composition as disclosed in the current specification relates to a composition that comprises lignin but may also in addition comprise additional components and/or elements e.g. as disclosed in the current specification. Thus, the "wood-derived lignin composition" may be considered as a "wood-derived lignin-containing composition" or a "wood-derived composition comprising lignin".

In the current specification the amounts of different components/elements in the wood-derived lignin composition are presented in weight-% based on the total dry matter content of the lignin composition. In this specification the term "total dry matter content of the lignin composition" may refer to the weight of the lignin composition as determined after removing the liquid from the lignin composition followed by drying the same at a temperature of 105° C. for 24 hours. The effectiveness of the liquid removal may be assessed by weighing the sample, drying for a further two hours at the specified temperature, and reweighing the sample. If the measured weights are the same, the drying has been complete and the total weight may be recorded.

As is clear to the skilled person, the total amount of the different components/elements in the wood-derived lignin composition may not exceed 100 weight-%. The amount in weight-% of the different components/elements in the wood-derived lignin composition may vary within the given ranges.

In one embodiment, a lignin composition comprising 0.5-6 weight-%, or 0.75-4 weight-%, or 1-3 weight-%, or 1.5-2 weight-%, of soluble components is provided.

Thus, the lignin composition may be obtained from subjecting a fraction comprising solid cellulose particles to an enzymatic hydrolysis process.

The inventors surprisingly found out that by the method as disclosed in the current specification, one is able to provide a wood-derived lignin composition, wherein the content of the soluble components in the lignin composition may be at most 2 weight-%, e.g. even below 1 weight-%. I.e. the method as disclosed in the current specification has the added utility of enabling the production of a high purity lignin composition.

In one embodiment, the lignin composition comprises acid soluble lignin in an amount of 0.5-2.5 weight-%, or 1-2 weight-% based on the total dry matter content of the lignin composition. The amount of acid-soluble lignin may be determined following a standard of TAPPI UM 250.

In one embodiment, the lignin composition comprises acid-insoluble lignin in an amount of 80-90 weight-%, or 82-90 weight-%, or 84-90 weight-%, or 87-90 weight-%, or 88-90 weight-%, based on the total dry matter content of the lignin composition.

The amount of acid-insoluble lignin may be determined following a modified standard of TAPPI T 222. I.e. the amount of acid-insoluble lignin may be determined gravimetrically by filtering in the following manner: A sample is treated with 72% sulfuric acid at constant temperature (30° C.) in a water bath for 1 h and it is autoclaved at 120° C., 1 bar for 1 h. The acid causes the lignin to precipitate and it can be determined gravimetrically. The precipitated lignin is separated by vacuum filtering the sample. The acid-insoluble lignin content of the sample in % may then be calculated using the following equation:

$$Lignin, \% = \frac{(M \times 100)}{W},$$

where M=weight of the acid-insoluble precipitation (g), and W=amount of dry sample (g).

In one embodiment, the average molecular weight of the lignin is 5500-12000 Da, or 6000-10000 Da. The average molecular weight may be determined with size exclusion chromatography (SEC) by using 0.1 M NaOH as eluent and a sample amount of about 1 mg/ml, which is dissolved in 0.1 M NaOH. The molecular weights are measured against polystyrenesulfonate standards. UV detector at wavelength of 280 nm is used. The expression "average molecular weight" should be understood in this specification, unless otherwise stated, as weight average molecular weight.

In one embodiment, the lignin composition comprises carbohydrates in an amount of 3-12 weight-%, or 4-9 weight-%, based on the total dry matter content of the lignin composition. The wood-derived lignin composition thus has a rather low carbohydrate content, which is an indication of high purity received for the produced wood-derived lignin composition.

The amount of carbohydrates may be determined following a standard of SCAN-CM 71:09.

In one embodiment, the lignin composition comprises nitrogen in an amount of 0.2-1.0 weight-%, or 0.4-0.8 weight-%, based on the total dry matter content of the lignin composition. The amount of nitrogen in the wood-derived lignin composition may be an indication of protein traces. The amount of nitrogen present in the lignin composition may be determined using any suitable method known to a person skilled in the art, e.g. the Kjeldahl method or catalytic thermal decomposition/chemiluminescence methods.

In one embodiment, the lignin composition comprises phenolic hydroxyl groups in an amount of 2.5-3.1 mmol/g, or 2.6-3.0 mmol/g.

In one embodiment, the lignin composition comprises aliphatic hydroxyl groups in an amount of 2.3-3.2 mmol/g, or 2.4-3.0 mmol/g.

Phenolic and aliphatic hydroxyl groups may be analysed by $^{31}$P NMR. Sample preparation for NMR analysis includes first dissolving lignin composition in dilute NaOH solution at pH 13.0 and temperature of 65° C., and consequently precipitating solubilised lignin with sulphuric acid at pH 3.0. The resulted solid material is thoroughly washed with water.

For NMR analyses, each lignin composition sample is accurately weighted (25 mg) and dissolved in N, N-dimethylformamide (150 μl) in a 4 ml vial. After total dissolution, pyridine (100 μl), internal standard solution (ISTD) (200 μl) endo-N-Hydroxy-5-norbornene-2,3-dicarboximide (e-HNDI, 0.005 mmol) in pyridine/CDCl3 (1.6/1, v/v) and Cr(acac)$_3$ solution (50 μl) (11.4 mg/1 ml) in pyridine/CDCl$_3$ (1.6/1, v/v) are added. Then, phosphitylation reagent (150 μl) 2-chloro-4,4,5,5-tetramethyl-1,3,2-dioxaphopholane [P.R. (II)] is added drop-wise. Finally, CDCl$_3$ (300 μl) is added to the solution and clear dark brown solution is achieved. Freshly prepared samples are measured with 31p NMR immediately after preparation at room temperature. Bruker 500 MHz NMR spectrometer is used for the measurement. Chemical shifts are reported relative to the sharp signal (132.2 ppm) originating from the reaction between water and P.R.II.

In one embodiment, the lignin composition comprises sulphur in an amount of 200-1000 ppm, or 300-700 ppm. The amount of sulphur may be determined according to standard SFS-EN ISO 11885 (2009) with microwave digestion and ICP-OES technique.

In one embodiment, the weight ratio of oxygen to carbon is 0.5-0.8, or 0.5-0.7, or 0.5-0.6.

The method for producing a wood-derived lignin composition as disclosed in the current specification fraction comprising solid comprises providing a cellulose particles, wherein the total dry matter content of the fraction comprising solid cellulose particles is 8-20 weight-%, and wherein the fraction comprising solid cellulose particles comprises at most 3 weight-% of wood shives of the size of wider than 1 mm. Providing such a fraction may comprise the following:

The fraction comprising solid cellulose particles may be provided starting e.g. from a wood-based feedstock originating from wood-based raw material and comprising wood chips, that is subjected to pretreatment to form a liquid fraction and a fraction comprising solid cellulose particles. By the expression "pretreating" or "pretreatment" should be understood in this specification, unless otherwise stated, (a) process(es) conducted to convert wood-based feedstock to a fraction comprising solid cellulose particles. As a result of the pretreatment, in addition to the fraction comprising solid cellulose particles, a liquid fraction may be formed. The liquid fraction may be separated from the fraction comprising solid cellulose particles. The fraction comprising solid cellulose particles may further include an amount of lignocellulose particles as well as lignin. Lignocellulose comprises lignin chemically bonded to the cellulose particles.

The wood-based raw material may be selected from a group consisting of hardwood, softwood, and their combination. The raw material may e.g. originate from pine, poplar, beech, aspen, spruce, eucalyptus, ash, or birch. The wood-based raw material may also be any combination or mixture of these. The wood-based raw material may be broadleaf wood. Preferably the wood-based raw material is broadleaf wood due to its relatively high inherent sugar content, but the use of other kinds of wood is not excluded. The broadleaf wood may be selected from a group consisting of beech, birch, ash, oak, maple, chestnut, willow, poplar, and any combination of mixture thereof.

In general, wood and wood-based raw materials are essentially composed of cellulose, hemicellulose, lignin, and extractives. Cellulose is a polysaccharide consisting of a chain of glucose units. Hemicellulose comprises polysaccharides, such as xylan, mannan, and glucan.

In one embodiment, the wood-derived lignin composition is a broadleaf-derived lignin composition. The wood-derived lignin composition may thus be produced from wood, such as broadleaf wood, hardwood, softwood, etc.

Providing the wood-based feedstock may comprise subjecting wood-based raw material to a mechanical treatment selected from debarking, chipping, dividing, cutting, beating, grinding, crushing, splitting, screening, and/or washing the wood-based raw material to form the wood-based feedstock.

Thus, providing the wood-based feedstock originating from the wood-based raw material may comprise subjecting the wood-based raw material to a mechanical treatment to form a wood-based feedstock. The mechanical treatment may comprise debarking, chipping, dividing, cutting, beating, grinding, crushing, splitting, screening, and/or washing the wood-based raw material. During the mechanical treatment e.g. wood logs can be debarked and/or wood chips of the specified size and structure can be formed. The formed wood chips can also be washed, e.g. with water, in order to remove e.g. sand, grit, and stone material therefrom. Further, the structure of the wood chips may be loosened before the pretreatment step. The wood-based feedstock may contain a certain amount of bark from the wood logs.

Providing the wood-based feedstock may comprise purchasing the wood-based feedstock. The purchased wood-based feedstock may comprise purchased wood chips or sawdust that originate from wood-based raw material.

Pretreatment of the wood-based feedstock may comprise different pretreatment steps. During the different pretreatment steps the wood-based feedstock as such changes. The aim of the pretreatment is to form a fraction comprising solid cellulose particles for further processing.

The pretreatment i) may comprise subjecting the wood-based feedstock to pre-steaming. The pretreatment may comprise subjecting the wood-based feedstock received from the mechanical treatment to pre-steaming. The pretreatment may comprise, an impregnation treatment and a steam explosion treatment and comprise, before subjecting the wood-based feedstock to impregnation treatment and thereafter to steam explosion treatment, subjecting the wood-based feedstock to pre-steaming. In one embodiment, pretreatment in i) comprises, before subjecting to the impregnation treatment, subjecting the wood-based feedstock to pre-steaming to form pre-steamed wood-based feedstock. The pre-steaming of the wood-based feedstock may be carried out with steam having a temperature of 100-130° C., at atmospheric pressure. During the pre-steaming the wood-based feedstock is treated with steam of low pressure. The pre-steaming may be also carried out with steam having a temperature of below 100° C., or below 98° C., or below 95° C. The pre-steaming has the added utility of reducing or removing air from inside of the wood-based feedstock. The pre-steaming may take place in at least one pre-steaming reactor.

Further, the pretreatment may comprise subjecting the wood-based feedstock to at least one impregnation treatment with an impregnation liquid. The impregnation treatment may be carried out to the wood-based feedstock received from the mechanical treatment and/or from the pre-steaming. The impregnation liquid may be selected from water, at least one acid, at least one alkali, at least one alcohol, or any combination or mixture thereof. In one embodiment pretreatment in i) comprises subjecting the wood-based feedstock to at least one impregnation treatment to form an impregnated wood-based feedstock.

The wood-based feedstock may be transferred from the mechanical treatment and/or from the pre-steaming to the impregnation treatment with a feeder. The feeder may be a screw feeder, such as a plug screw feeder. The feeder may compress the wood-based feedstock during the transfer. When the wood-based feedstock is then entering the impregnation treatment, it may become expanded and absorbs the impregnation liquid.

The impregnation liquid may comprise water, at least one acid, at least one alkali, at least one alcohol, or any combination or mixture thereof. The at least one acid may be selected from a group consisting of inorganic acids, such as sulphuric acid ($H_2SO_4$), nitric acid, phosphoric acid; organic acids, such as acetic acid, lactic acid, formic acid, carbonic acid; and any combination or mixture thereof. In one embodiment, the impregnation liquid comprises sulphuric acid, e.g. dilute sulphuric acid. The concentration of the acid may be 0.3-5.0% w/w, 0.5-3.0% w/w, 0.6-2.5% w/w, 0.7-1.9% w/w, or 1.0-1.6% w/w. The impregnation liquid may act as a catalyst in affecting the hydrolysis of the hemicellulose in the wood-based feedstock. In one embodiment, the impregnation is conducted by using only water, i.e. by autohydrolysis. In one embodiment, the wood-based feedstock may be impregnated through alkaline hydrolysis. The alkali used in the alkaline hydrolysis may be any metal hydroxide. NaOH, KOH, and $Ca_2(OH)_3$ can be mentioned as examples to be used as the alkali in the alkaline hydrolysis.

The impregnation treatment may be conducted in at least one impregnation reactor or vessel. In one embodiment, two or more impregnation reactors are used. The transfer from one impregnation reactor to another impregnation reactor may be carried out with a screw feeder.

The impregnation treatment may be carried out by conveying the wood-based feedstock through at least one impregnation reactor that is at least partly filled with the impregnation liquid, i.e. the wood-based feedstock may be transferred into the impregnation reactor, where it sinks into the impregnation liquid, and transferred out of the impregnation reactor such that the wood-based feedstock is homogenously impregnated with the impregnation liquid. As a result of the impregnation treatment, impregnated wood based feedstock is formed. The impregnation treatment may be carried out as a batch process or in a continuous manner.

The residence time of the wood-based feedstock in an impregnation reactor, i.e. the time during which the wood-based feedstock is in contact with the impregnation liquid, may be 5 seconds-5 minutes, or 0.5-3 minutes or about 1 minute. The temperature of the impregnation liquid may be e.g. 20-99° C., or 40-95° C., or 60-93° C. Keeping the temperature of the impregnation liquid below 100° C. has the added utility of hindering or reducing hemicellulose from dissolving.

After the impregnation treatment, the impregnated wood-based feedstock may be allowed to stay in e.g. a storage tank or a silo for a predetermined period of time to allow the impregnation liquid absorbed into the wood-based feedstock to stabilize. This predetermined period of time may be 15-60 minutes, or e.g. about 30 minutes.

In one embodiment, the wood-based feedstock is subjected to an impregnation treatment with dilute sulphuric acid having a concentration of 1.32% w/w and a temperature of 92° C.

Pretreatment may comprise subjecting the wood-based feedstock to steam explosion treatment. The wood-based feedstock from the impregnation treatment may be subjected to steam explosion treatment. I.e. pretreatment may comprise subjecting the impregnated wood-based feedstock to steam explosion treatment to form a steam-treated wood-based feedstock.

In one embodiment, pretreatment comprises mechanical treatment of wood-based material to form a wood-based feedstock, the pre-steaming of the wood-based feedstock to form pre-steamed wood-based feedstock, impregnation treatment of the pre-steamed wood-based feedstock to form impregnated wood-based feedstock, and the steam explosion treatment of the impregnated wood-based feedstock. In one embodiment, pretreatment comprises pre-steaming the wood-based feedstock, impregnation treatment of the pre-steamed wood-based feedstock, and steam explosion treatment of the impregnated wood-based feedstock. In one embodiment, pretreatment comprises impregnation treatment of the wood-based feedstock, and steam explosion treatment of the impregnated wood-based feedstock. I.e. the wood-based feedstock having been subjected to the impregnation treatment may thereafter be subjected to the steam explosion treatment. Also, the wood-based feedstock having been subjected to pre-steaming, may then be subjected to the impregnation treatment and thereafter the impregnated wood-based feedstock having been subjected to the impregnation treatment may be subjected to steam explosion treatment.

The wood-based feedstock can be stored in e.g. chip bins or silos between the different treatments. Alternatively, the wood-based feedstock may be conveyed from one treatment to the other in a continuous manner.

In one embodiment, pretreatment in i) comprises subjecting the impregnated wood-based feedstock to steam explosion treatment to form a steam-treated wood-based feedstock. The pretreatment may comprise subjecting the impregnated wood-based feedstock to steam explosion treatment that carried out by treating the is impregnated wood-based feedstock with steam having a temperature of 130-240° C., or 180-200° C., or 185-195° C., under a pressure of 0.17-3.25 MPaG followed by a sudden, explosive decompression of the wood-based feedstock. The impregnated wood-based feedstock may be treated with the steam for 1-20 minutes, or 1-20 minutes, or 2-15 minutes, or 4-13 minutes, or 3-10 minutes, or 3-8 minutes, before the sudden, explosive decompression of the steam-treated wood-based feedstock.

In this specification, the term "steam explosion treatment" may refer to a process of hemihydrolysis in which the feedstock is treated in a reactor (steam explosion reactor) with steam having a temperature of 130-240° C., or 180-200° C., or 185-195° C., under a pressure of 0.17-3.25 MPaG followed by a sudden, explosive decompression of the feedstock that results in the rupture of the fiber structure of the feedstock.

The steam explosion treatment may be conducted in a pressurized reactor. The steam explosion treatment may be carried out in the pressurized reactor by treating the impregnated wood-based feedstock with steam having a temperature of 130-240° C., or 180-200° C., or 185-195° C., under a pressure of 0.17-3.25 MPaG followed by a sudden, explosive decompression of the feedstock. The impregnated wood-based feedstock may be introduced into the pressurized reactor with a compressing conveyor, e.g. a screw feeder. During transportation with the screw feeder, if used, the acid in liquid form is removed, a part of the impregnation liquid absorbed by the wood-based feedstock is removed as a pressate while most of it remains in the feedstock. The impregnated wood-based feedstock may be introduced into the pressurized reactor along with steam and/or gas. The pressure of the pressurized reactor can be controlled by the addition of steam. The pressurized reactor may operate in a continuous manner or as a batch process. The impregnated wood-based feedstock, e.g. the wood-based feedstock that has been subjected to an impregnation treatment, may be introduced into the pressurized reactor at a temperature of 25-140° C. The residence time of the feedstock in the pressurized reactor may be 0.5-120 minutes. The term "residence time" should in this specification, unless otherwise stated, be understood as the time between the feedstock being introduced into or entering e.g. the pressurized reactor and the feedstock being exited or discharged from the same.

The impregnated feedstock entering the pressurized reactor may be soaked with impregnation liquid, such as sulfuric acid. In one embodiment, the amount of sulphuric acid in the steam explosion treatment may be 0.10-0.75 weight-% based on the total dry matter content of the wood-based feedstock. The amount of acid present in the steam explosion treatment may be determined by measuring the sulphur content of the liquid of the steam-treated wood-based feedstock or the liquid part of the steam-treated wood-based feedstock after steam explosion treatment. The amount of sulphuric acid in the steam explosion reactor may be determined by subtracting the amount of sulphur in the wood-based feedstock from the measured amount of total sulphur in the steam-treated wood-based feedstock.

As a result of the hemihydrolysis of the wood-based feedstock affected by the steam explosion treatment in the reactor, the hemicellulose present in the wood-based feedstock may become hydrolyzed or degraded into e.g. xylose oligomers and/or monomers. The hemicellulose comprises polysaccharides such as xylan, mannan and glucan. Xylan is thus hydrolyzed into xylose that is a monosaccharide. In one embodiment, the conversion of xylan present in the wood-based feedstock into xylose as a result of the hemihydrolysis is 87-95%, or 83-93% or 90-92%.

Thus, steam explosion treatment of the feedstock may result in the formation of an a steam-treated wood-based feedstock. The steam-treated wood-based feedstock from the steam explosion may be subjected to steam separation. The steam-treated wood-based feedstock from the steam explosion treatment may be mixed or combined with a liquid, e.g. water. The steam-treated wood-based feedstock from the steam explosion treatment may be mixed with a liquid to form a slurry. The liquid may be pure water or water containing C5 sugars. The water containing C5 sugars may be recycled water from separation and/or washing the fraction comprising solid cellulose particles before enzymatic hydrolysis. The steam-treated wood-based feedstock may be mixed with the liquid and the resulting mass may be homogenized mechanically to break up agglomerates. The slurry may comprise a liquid phase and a solid phase. The slurry may comprise solid cellulose particles.

In one embodiment, pretreatment in i) comprises mixing the steam-treated wood-based feedstock with a liquid to form a slurry.

A liquid fraction and a fraction comprising solid cellulose particles may be separated from the slurry, e.g. by a solid-liquid separation process. The solid-liquid separation process may comprise washing. The washing may be continued until the amount of soluble organic components in the fraction comprising solid cellulose particles is 0.5-5 weight-%, or 1-4 weight-%, or 1.5-3 weight-% based on the total dry matter content.

The solid-liquid separation process may be carried out by displacement washing or countercurrent washing.

Displacement washing, or replacement washing as it may also be called, is a method for separating solids and liquid from each other by the use of a rather minor amount of washing liquid. Thus, displacement washing may be considered as an operation by which it is possible to wash solid particles with a minimum amount of washing liquid, such as water.

In countercurrent washing, the movement of the fraction comprising solid cellulose particles is generally in a forward direction, whereas the washing liquid, such as water, flows in the opposite direction. As for the displacement washing, also the countercurrent washing may reduce the consumption of washing liquid to a great extent.

The countercurrent washing may comprise at least two solid-liquid separation steps and one dilution in between the steps with washing solution. The washing solution may be clean water. The amount of water needed may vary depending on how many solid-liquid separation steps are performed in total, the total dry matter content in the feed of the solid-liquid separation step and the total dry matter content in the fraction comprising solid cellulose particles after each solid-liquid separation step.

The washing liquid may be fresh washing water or recycled washing water. The washing water may be fresh water, drinking water, or a sugar containing liquid with low sugar content. The conductivity of the washing liquid may be about 0.1 mS/cm.

The ratio of the used washing liquid to the solids may be 0.5:1-8:1 (w/w), or 0.5:1-5:1 (w/w), or 0.5:1-3:1 (w/w), or 0.5:1-2:1 (w/w) in the case of displacement washing.

The progression of the displacement washing as well as of the countercurrent washing may be monitored by measuring the conductivity of the liquid fraction recovered from this treatment. Once the conductivity of the liquid fraction is below or equal to a predetermined threshold value of 0.35 mS/cm, one may conclude that that the desired amount of the C5 sugars and other soluble impurities have been removed and the washing may be concluded. In one embodiment, the washing is continued until the conductivity of the liquid fraction is 0.1-1.0 mS/cm or 0.2-0.5 mS/cm.

As a result of washing, a fraction comprising solid cellulose particles having a total dry matter content of 15-50 weight-% is formed. In one embodiment, a fraction comprising solid cellulose particles having a total dry matter content of 15-50 weight-%, or 21-40 weight-%, or 25-40 weight-%, or 30-40 weight-%, or 35-40 weight-% is formed.

The separated fraction comprising solid cellulose particles may be diluted to a total dry matter content of 8-20 weight-%, or 10-18 weight-%, or 15-16 weight-%. Thus, if needed, the separated fraction comprising solid cellulose particles may be diluted in step i). The need to dilute is dependent on the total dry matter content that the fraction comprising solid cellulose particles may have as a result of the above described separation step. I.e. if the total dry matter content of the fraction comprising solid cellulose particles as a result of the above described separation step is higher than 20 weight-%, then the fraction comprising solid cellulose particles may be diluted. If the total dry matter content of the fraction comprising solid cellulose particles as a result of the above described separation step is 8-20 weight-%, then no dilution may be needed. The fraction comprising solid cellulose particles may be diluted with water and/or other liquid containing at least soluble carbohydrates. In one embodiment, the fraction comprising solid cellulose particles may be diluted in step i) with water to a total dry matter content of 8-20 weight-%, or 10-18 weight-%, or 15-16 weight-%.

The liquid fraction may comprise sugars from hydrolyzed hemicellulose as well as soluble lignin and other by-products. In one embodiment, the liquid fraction comprises carbohydrates, such as C5 sugars ($C_5H_{10}O_5$ or ($C_5(H_2O)_n$). The liquid fraction may comprise carbohydrates, such as monosaccharides ($C_6H_{12}O_6$ or $C_5H_{10}O_5$), disaccharides ($C_{12}H_{22}O_{11}$), oligosaccharides and/or polysaccharides (($C_6H_{10}O_5)_n$ or ($C_5H_8O_4)_n$). In one embodiment, the liquid fraction comprises soluble C5 carbohydrates ($C_5H_{10}O_5$ or $C_5(H_2O)_n$) and other carbohydrates. The liquid fraction may comprise also other components.

The fraction comprising solid cellulose particles may, in addition to cellulose, comprise lignin. In one embodiment, the fraction comprising solid cellulose particles comprises carbohydrates, e.g. solid C6 carbohydrates ($C_6H_{12}O_6$ or $C_6(H_2O)$), and lignin. The fraction comprising solid cellulose particles may also comprise other carbohydrates and other components.

In one embodiment, subjecting the wood-based feedstock to pretreatment comprises:

pre-steaming of the wood-based feedstock at atmospheric pressure with steam having a temperature of 100-130° C.;

subjecting the pre-steamed feedstock to an impregnation treatment with an impregnation liquid comprising sulphuric acid having a concentration of 0.3-5.0% w/w, or 0.5-3.0% w/w, or 0.6-2.5% w/w, or 0.7-1.9% w/w, or 1.0-1.6% w/w, and a temperature of 20-99° C., or 40-95° C., or 60-93° C.;

subjecting the impregnated wood-based feedstock to steam explosion treatment carried out by treating the impregnated wood-based feedstock with steam having a temperature of 130-240° C., or 180-200° C., or 185-195° C. followed by a sudden, explosive decompression of the wood-based feedstock;

mixing the steam-treated wood-based feedstock with a liquid to form a slurry;

separating the slurry into a liquid fraction and a fraction comprising solid cellulose particles.

Thus, a fraction comprising solid cellulose particles is provided wherein the fraction comprising solid cellulose particles comprises at most 3 weight-% of wood shives of the size of wider than 1 mm as determined by the Somerville method. In one embodiment, the total dry matter content of the fraction comprising solid cellulose particles is 8-20 weight-%, or 10-18 weight-%, or 15-16 weight-%. The inventors surprisingly found out that the total dry matter content of the fraction comprising solid cellulose particles being 8-20 weight-% when subjecting the same to the enzymatic hydrolysis process in ii) has the added utility of enhanced conversion efficiency. If the total dry matter content in the fraction going to the enzymatic hydrolysis is too high, the mixing in the enzymatic hydrolysis reactors may be poor and the conversion of cellulose to carbohydrates may be low.

This may then increase the amount of unwanted carbohydrates in the lignin. The specified total dry matter content may be maintained at the essentially same level through the enzymatic hydrolysis process, i.e. through the first enzymatic hydrolysis step and the second enzymatic hydrolysis step, as well as the pre-hydrolysis step if used.

The pretreatment as discussed above may affect the size of the wood shives. At most 3 weight-% of the wood shives in the fraction comprising solid cellulose particles may be wider than 1 mm as determined by the Somerville method when the fraction comprising solid cellulose particles is subjected to the following enzymatic hydrolysis. A larger amount of shives may adversely affect the lignin.

Step ii) comprises subjecting the fraction comprising solid cellulose particles from i) to an enzymatic hydrolysis process. As is commonly known, enzymes used for enzymatic hydrolysis contain nitrogen. When subjecting the fraction comprising solid cellulose particles from i) to an enzymatic hydrolysis process, the amount of nitrogen entering with the enzymes to the enzymatic hydrolysis process may be adjusted to 0.05-0.6 weight-% based on the total dry matter content of the fraction comprising solid cellulose particles. In one embodiment, the amount of nitrogen that is entering with the enzymes into the enzymatic hydrolysis process is adjusted to 0.05-0.6 weight-%, or 0.1-0.5 weight-%, or 0.15-0.4 weight-%, based on the total dry matter content of the fraction comprising solid cellulose particles.

The amount of nitrogen entering the enzymatic hydrolysis process may be adjusted by adjusting the amount of enzyme that is used. Depending on the selected enzyme and the concentration of the enzyme composition used, one is able to determine the amount of nitrogen and thus the amount of enzyme to be used in the enzymatic hydrolysis process.

The inventors surprisingly found out that the total amount of enzyme used for producing the wood-derived lignin composition may be essentially reduced in the enzymatic hydrolysis process compared to prior known processes. Being able to reduce the total amount of enzyme to be used does not only affect the production costs and stages but affects also the end product produced, i.e. a high purity wood-based lignin composition may be produced.

The inventors surprisingly found out that when providing a fraction comprising solid cellulose particles, wherein the total dry matter content of the fraction comprising solid cellulose particles is 8-20 weight-%, and wherein the fraction comprising solid cellulose particles comprises at most 3 weight-% of wood shives of the size of wider than 1 mm, the total amount of enzymes needed during the enzymatic hydrolysis process may be reduced. The inventors thus surprisingly found out that the fraction comprising solid cellulose particles thus has properties that may enable the used enzymes to efficiently convert the sugars present during the enzymatic hydrolysis process even with a low amount of enzymes. Further, for the quality of the produced lignin composition it may be important that not too much of shives are entering into the enzymatic hydrolysis with the cellulose.

In one embodiment, the enzymatic hydrolysis process ii) comprises a pre-hydrolysis step before the first enzymatic hydrolysis step iia), wherein the fraction comprising solid cellulose particles is subjected to a pre-hydrolysis step for 1-2 hours, during which the pH is kept at a pH value of 3.5-6.5, or 4.0-6.0, or 4.5-5.5. The pre-hydrolyzed fraction comprising solid cellulose particles may then as such be directly subjected to the first enzymatic hydrolysis step. I.e. no separation or purification steps may be used between the pre-hydrolysis step and the first enzymatic hydrolysis step. In one embodiment, the viscosity of the fraction comprising solid cellulose particles is 2000-7000 mPas before being subjected to the pre-hydrolysis step. In one embodiment, the viscosity of the fraction comprising solid cellulose particles is decreased by at least 70%, or at least 75%, or at least 80%, during the pre-hydrolysis step. I.e. the pre-hydrolysis step may result in a reduction of at least 70%, or at least 75%, or at least 80%, of the viscosity of the fraction comprising solid cellulose particles compared to the viscosity of the fraction before being subjected to the pre-hydrolysis step. The viscosity may be determined by Brookfield viscometer (10 rpm, spindle type Vane, spindle size 73) at 12% suspended solids content and at a temperature of 50° C.

In one embodiment, the first enzymatic hydrolysis step and/or the second enzymatic hydrolysis step are/is carried out at a temperature 30-70° C., or 35-65° C., or 40-60° C., or 42-59° C., or 45-58° C., or 47-57° C. while keeping the pH of the fraction comprising solid cellulose particles at a pH value of 3.5-6.5, or 4.0-6.0, or 4.5-5.5.

In one embodiment, the first enzymatic hydrolysis step is allowed to continue for 24-72 hours, or 25-40 hours, or 28-31 hours.

In one embodiment, the second enzymatic hydrolysis step is allowed to continue for 24-72 hours, or 32-65 hour, or 35-50 hours, or 38-47 hours.

The enzymes are catalysts for the enzymatic hydrolysis. The enzymatic reaction decreases the pH and by shortening the length of the cellulose fibers it may also decrease the viscosity. Subjecting the fraction comprising solid cellulose particles to enzymatic hydrolysis may result in cellulose being transformed into glucose monomers with enzymes. Lignin present in the fraction comprising solid cellulose particles may remain essentially in solid form.

At least one enzyme may be used for carrying out the enzymatic hydrolysis. The at least one enzyme may be selected from a group consisting of cellulases, hemicellulases, laccases, and lignolytic peroxidases. Cellulases are multi-protein complexes consisting of synergistic enzymes with different specific activities that can be divided into exo- and endo-cellulases (glucanase) and β-glucosidase (cellobiose). The enzymes may be either commercially available cellulase mixes or onsite manufactured.

If pre-hydrolysis step is used then the enzymes needed in the enzymatic hydrolysis process in ii), may be added only in the pre-hydrolysis step.

Cellulose is an insoluble linear polymer of repeating glucose units linked by β-1-4-glucosidic bonds. During the enzymatic hydrolysis, cellulose chains are broken by means of breaking at least one β-1-4-glucosidic bond.

In one embodiment, the solid fraction comprising lignin from the enzymatic hydrolysis process of ii) is subjected to at least one, or at least two, or at least three, purification processes. Each of the at least one purification processes may comprise re-slurring the solid fraction comprising lignin and thereafter subjecting the formed slurry to a solid-liquid separation process. The solid fraction comprising lignin may be re-slurried with a dilution liquid such as water. The re-slurried lignin fraction may then be subjected to solid-liquid separation process. The dilution liquid received from the solid-liquid separation may be recirculated to the pre-hydrolysis step and/or to step iic) of reslurrying the separated solid fraction comprising lignin from iib).

The solid-liquid separation as described in the current specification, such as the first solid-liquid separation process and the second solid-liquid separation process, may be carried out by countercurrent washing, displacement washing, filtration, decanting, and/or by centrifugal treatment. The filtration may be vacuum filtration, filtration based on the use of reduced pressure, filtration based on the use of overpressure, or filter pressing. The decanting may be repeated in order to improve separation. The solid-liquid separation may be carried out with a decanter centrifuge. In one embodiment, the first solid-liquid separation process and/or the second solid-liquid separation process is carried out by filtration, decanting, and/or by centrifugal treatment.

The separated solid fraction comprising lignin from step iib) may be re-slurried in step iic) with a liquid. The liquid may be e.g. water. The liquid may be recycled dilution liquid from a purification process.

The method as disclosed in the current specification has the added utility of providing a wood-derived lignin composition with a high content of lignin. The wood-derived lignin composition has the added utility of fulfilling purity properties required for further use in e.g. composites and fillers.

EXAMPLES

Reference will now be made in detail to the embodiments of the present disclosure, an example of which is illustrated in the accompanying drawing.

The description below discloses some embodiments in such a detail that a person skilled in the art is able to utilize the method based on the disclosure. Not all steps of the embodiments are discussed in detail, as many of the steps will be obvious for the person skilled in the art based on this disclosure.

For reasons of simplicity, item numbers will be maintained in the following exemplary embodiments in the case of repeating components.

The enclosed FIG. 1 illustrates an embodiment of a flow chart of the method for producing a wood-derived lignin composition in some detail. The method for producing a wood-derived lignin of FIG. 1 composition comprises providing a fraction comprising solid cellulose particles, wherein the total dry matter content of the fraction comprising solid cellulose particles is 8-20 weight-%, and wherein the fraction comprising solid cellulose particles comprises at most 3 weight-% of wood shives of the size of wider than 1 mm as determined by the Somerville method.

The fraction comprising solid cellulose particles may be provided e.g. from a wood-based feedstock originating from wood-based raw material and comprising wood chips, that is subjected to pretreatment to form a liquid fraction and a fraction comprising solid cellulose particles (step i) of FIG. 1). The liquid fraction and the fraction comprising solid cellulose particles may be then separated e.g. by a solid-liquid separation process.

The provided fraction comprising solid cellulose particles is then subjected to a first enzymatic hydrolysis step for 8-72 hours to form a first hydrolysis product (step iia) of FIG. 1). The first hydrolysis product is then separated into a solid fraction comprising lignin and a liquid carbohydrate fraction iib). The separated solid fraction comprising lignin is then re-slurried (step iic) of FIG. 1). The re-slurried solid fraction comprising lignin is then subjected to a second enzymatic hydrolysis step in iid) for 8-72 hours to form a second hydrolysis product, which are then separated e.g. by a second solid-liquid separation process into a liquid carbohydrate fraction and a solid fraction comprising lignin (step iid) of FIG. 1). The solid fraction comprising lignin from the enzymatic hydrolysis process of ii) is then subjected to at least one purification process to provide the lignin composition (step iii) of FIG. 1).

Example 1—Producing Wood-Derived Lignin Composition

In this example a wood-derived lignin composition was prepared.

First a wood-based feedstock comprising chips of beech wood was provided. The wood-based feedstock was then subjected to pretreatment in the following manner:

The wood-based feedstock was subjected to pre-steaming. Pre-steaming of the wood-based feedstock was carried out at atmospheric pressure with steam having a temperature of 100° C. for 180 minutes. The pre-steamed feedstock was then subjected to an impregnation treatment with dilute sulphuric acid having a concentration of 1.32% w/w and a temperature of 92° C. The pre-steamed wood-based feedstock was allowed to be affected by the impregnation liquid for 30 minutes. The impregnated wood-based feedstock was then subjected to steam explosion treatment. The steam explosion treatment was carried out by treating the impregnated wood-based feedstock with steam having a temperature of 191° C. under at atmospheric pressure followed by a sudden, explosive decompression of the wood-based feedstock. The amount of sulphuric acid in steam explosion reactor was 0.33 weight-% based on the total dry matter content of the wood-based feedstock. In the determination of the amount of sulphuric acid the sulphur content of wood was 0.02 weight-% based on the total dry matter content of the wood used.

In the pretreatment, the conversion of xylan in the wood-based feedstock into xylose was 91% and the ratio of solubilized glucose to solubilized xylose was approximately 0.15 as determined by HPLC-RI. The steam-treated wood-based feedstock was then mixed with water in a mixing vessel to form a slurry.

The slurry was then separated into a liquid fraction and a fraction comprising solid cellulose particles by a solid-liquid separation process, which in this example was countercurrent washing. The fraction comprising solid cellulose particles also comprised lignin.

The total dry matter content of the fraction comprising solid cellulose particles was 30 weight-%. It was also checked that at most 3 weight-% of the wood shives in the fraction comprising solid cellulose particles were wider than 1 mm as determined by the Somerville method.

The fraction comprising solid cellulose particles was then diluted with water to a total dry matter content of approximately 13 weight-% and subjected to a first enzymatic hydrolysis step in a batch reactor by using the following conditions:

initial pH=5.0 adjusted by NaOH
enzyme=Commercially available cellulase mixture
amount of nitrogen entering the reactor with enzymes=0.375%
enzyme solution loading=6.5 weight-% based on the total dry matter content
residence time=40 hours
temperature=47-52° C. during the process A first hydrolysis product was formed from the first hydrolysis step. The first hydrolysis product was then separated into a solid fraction comprising lignin and a liquid carbohydrate fraction by a first solid-liquid separation process, i.e. by separating from each other by using a decanter centrifuge.

The separated solid fraction comprising lignin was then re-slurried by mixing the same with water to a total dry matter content of 13 weight-%.

The re-slurried solid fraction comprising lignin was then subjected to a second hydrolysis step without any enzyme addition in a batch reactor by using the following conditions:

initial pH=5.0 adjusted by NaOH
residence time=60 hours
temperature=47-52° C. during the process A second hydrolysis product was formed from the second hydrolysis step. The second hydrolysis product was then separated into a solid fraction comprising lignin and a liquid carbohydrate fraction by a second solid-liquid separation process, i.e. by separating from each other by using a decanter centrifuge in a two-step process. As a last step the separation further comprised a filter press.

The solid fraction comprising lignin was then subjected to a purification process comprising countercurrent washing, wherein the washing liquid was water, to provide the lignin composition.

The wood-derived lignin composition was then analyzed according to TAPPI 222 method and the carbohydrates were analyzed by HPLC-RI using a Waters e2695 Alliance Separation module, a Waters 2998 Photodiode Array, and a Waters 2414 Refractive Index detector. Separation was achieved with a Bio-Rad Aminex HPX-87 column with dimensions 300 mm×7.8 mm equipped with Micro-Guard Deashing and Carbo-P guard columns in series. Ultrapure water was used as eluent. The results are presented in the below table:

| Acid-insoluble lignin, gravimetrically determined | weight % of total dry matter content | 84.9 |
|---|---|---|
| Average molecular weight of lignin, SEC | Da | 6720 |
| Carbohydrates, acid hydrolysis | mg/g | 75.4 |
| Total nitrogen, Kjeldhal | mg/kg | 6045.9 |
| weight ratio oxygen to carbon | | 0.56 |
| phenolic hydroxyl groups | mmol/g | 2.8 |
| aliphatic hydroxyl groups | mmol/g | 2.5 |
| Sulphur, S, ICP | mg/kg | 384 |

It is obvious to a person skilled in the art that with the advancement of technology, the basic idea may be implemented in various ways. The embodiments are thus not limited to the examples described above; instead they may vary within the scope of the claims.

The embodiments described hereinbefore may be used in any combination with each other. Several of the embodiments may be combined together to form a further embodiment. A wood-derived lignin composition or a method disclosed herein, may comprise at least one of the embodiments described hereinbefore. It will be understood that the benefits and advantages described above may relate to one embodiment or may relate to several embodiments. The embodiments are not limited to those that solve any or all of the stated problems or those that have any or all of the stated benefits and advantages. It will further be understood that reference to 'an' item refers to one or more of those items. The term "comprising" is used in this specification to mean including the feature(s) or act(s) followed thereafter, without excluding the presence of one or more additional features or acts.

The invention claimed is:

1. A hardwood-derived lignin composition comprising:
acid-insoluble lignin in an amount of 80-90 weight-% based on the total dry matter content of the lignin composition, wherein the average molecular weight of the lignin is 5000-15000 Da;

carbohydrates in an amount of 1.5-15 weight-% based on the total dry matter content of the lignin composition; 0.5-6 weight-% of soluble components; and
nitrogen in an amount of 0.2-1.5 weight-% based on the total dry matter content of the lignin composition, wherein weight ratio of oxygen to carbon is 0.5-0.8, and
wherein the lignin composition is obtained from subjecting a fraction comprising solid cellulose particles to an enzymatic hydrolysis process.

2. The hardwood-derived lignin composition of claim 1, wherein the lignin composition comprises acid-insoluble lignin in an amount of 82-90 weight-%, based on the total dry matter content of the lignin composition.

3. The hardwood-derived lignin composition of claim 1, wherein the average molecular weight of the lignin is 5500-12000.

4. The hardwood-derived lignin composition of claim 1, wherein the lignin composition comprises carbohydrates in an amount of 3-12 weight-%, based on the total dry matter content of the lignin composition.

5. The hardwood-derived lignin composition of claim 1 wherein the lignin composition comprises nitrogen in an amount of 0.2-1.0 weight-%, based on the total dry matter content of the lignin composition.

6. The hardwood-derived lignin composition of claim 1, wherein the lignin composition comprises phenolic hydroxyl groups in an amount of 2.5-3.1 mmol/g.

7. The hardwood-derived lignin composition of claim 1, wherein the lignin composition comprises aliphatic hydroxyl groups in an amount of 2.3-3.2 mmol/g.

8. The hardwood-based lignin composition of claim 1, wherein the lignin composition comprises sulphur in an amount of 200-1000 ppm.

9. A method for producing a hardwood-derived lignin composition, wherein the method comprises:
i) providing a wood-based feedstock originating from wood-based raw material and comprising wood chips, wherein the wood-based raw material is hardwood, and subjecting the wood-based feedstock to pretreatment to form a fraction comprising solid cellulose particles, wherein pretreatment comprises subjecting the wood-based feedstock to at least one impregnation treatment to form an impregnated wood-based feedstock, subjecting the impregnated wood-based feedstock to steam explosion treatment to form a steam-treated wood-based feedstock, mixing the steam-treated wood-based feedstock with a liquid to form a slurry, and separating a liquid fraction and a fraction comprising solid cellulose particles from the slurry,
wherein the total dry matter content of the fraction comprising solid cellulose particles is 8-20 weight-%, and wherein at most 3 weight-% of the wood shives in the fraction comprising solid cellulose particles are wider than 1 mm as determined by the Somerville method;
ii) subjecting the fraction comprising solid cellulose particles from i) to an enzymatic hydrolysis process, wherein the amount of nitrogen that is entering with the enzymes into the enzymatic hydrolysis process is adjusted to 0.05-0.6 weight-%, based on the total dry matter content of the fraction comprising solid cellulose particles, and wherein the enzymatic hydrolysis process comprises:
iia) subjecting the fraction comprising solid cellulose particles to a first enzymatic hydrolysis step for 8-72 hours to form a first hydrolysis product;

iib) separating the first hydrolysis product into a solid fraction comprising lignin and a liquid carbohydrate fraction by a first solid-liquid separation process;

iic) re-slurrying the separated solid fraction comprising lignin from iib) by mixing it with a liquid;

iid) subjecting the re-slurried solid fraction comprising lignin to a second enzymatic hydrolysis step for 8-72 hours to form a second hydrolysis product;

iie) separating the second hydrolysis product into a solid fraction comprising lignin and a liquid carbohydrate fraction by a second solid-liquid separation process; and iii) subjecting the solid fraction comprising lignin from the enzymatic hydrolysis process of ii) to at least one purification process to provide the lignin composition, wherein the at least one purification process in step iii) is continued until a lignin composition comprising 0.5-6 weight-% of soluble components is provided.

10. The method of claim 9, wherein each of the at least one purification processes comprises re-slurring the solid fraction comprising lignin and thereafter subjecting the formed slurry to a solid-liquid separation process.

11. The method of claim 9, wherein the total dry matter content of the fraction comprising solid cellulose particles is 10-18 weight-%.

12. The method of claim 9, wherein the enzymatic hydrolysis process ii) comprises a pre-hydrolysis step before the first enzymatic hydrolysis step iia), wherein the fraction comprising solid cellulose particles is subjected to a pre-hydrolysis step for 1-2 hours, during which the pH is kept at a pH value of 3.5-6.5.

13. The method of claim 12, wherein the pre-hydrolyzed fraction comprising solid cellulose particles is as such directly subjected to the first enzymatic hydrolysis step.

14. The method of claim 1, wherein the first enzymatic hydrolysis step and/or the second enzymatic hydrolysis step are/is carried out at a temperature 30-70° C., while keeping the pH of the fraction comprising solid cellulose particles at a pH value of 3.5-6.5.

15. The method of claim 9, wherein the first enzymatic hydrolysis step is allowed to continue for 24-72 hours.

16. The method of claim 9, wherein the second enzymatic hydrolysis step is allowed to continue for 24-72 hours.

* * * * *